United States Patent [19]
Erlander et al.

[11] Patent Number: 6,107,476
[45] Date of Patent: Aug. 22, 2000

[54] NUCLEIC ACID MOLECULE ENCODING A PROTEIN GROWTH FACTOR FOR INHIBITING PROSTATE CANCER CELL GROWTH

[75] Inventors: Mark G. Erlander, Encinitas; Shaoming Huang; Michael A. Jackson, both of Del Mar, all of Calif.; Per A. Peterson, Bedminster, N.J.

[73] Assignee: Ortho-McNeil Pharmaceutical, Inc., Raritan, N.J.

[21] Appl. No.: 08/927,433

[22] Filed: Sep. 11, 1997

Related U.S. Application Data

[60] Provisional application No. 60/025,923, Sep. 11, 1996.

[51] Int. Cl.[7] .............................. C07H 21/04; C07H 21/02
[52] U.S. Cl. ...................... 536/23.51; 536/23.5; 536/23.1
[58] Field of Search ............................. 514/44; 424/93.2, 424/93.21; 435/320.1; 536/23.1, 23.5, 23.51

[56] References Cited

U.S. PATENT DOCUMENTS 4,886,747  12/1989  Derynck et al. .................. 435/69.4

FOREIGN PATENT DOCUMENTS

| | | |
|---|---|---|
| 0 319 944 A2 | 7/1998 | European Pat. Off. . |
| 7-250688 | 10/1995 | Japan . |
| 7-258293 | 10/1995 | Japan . |

OTHER PUBLICATIONS

Ross et al. 91996) Human Gene Therapy 7m 1781–1790.
Verma et al. (1997) Nature 389, 239–242.
Miller et al. 91995) FASEB Journal 9, 190–199.
Crystal (1995) Science 270, 404–410.
Blau et al (Nov. 2, 1995) New Eng. J. Med., pp. 1204–1207.
J. Massague, Ann, Rev. Cell. Biol., 1990,6:597–641, The Transforming Growth Factor –β Family.
N. M. Greenberg, et al., P.N.A.S. U.S.A. 92:3439–3443 (1995), Prostate Concer in a Transgenic Mouse.
T. C. Thompson, et al., Cancer 71: 1165–1171 (1993) Transgenic Models for the Study of Prostate Cancer.
Usui et al, J. Neurosci.,14(8): 4915–4926, 1994 Isolation of Clones of Rat Striatum–Specific mRNAs.
Altschul et. al., J.Mol.Biol., 215:40, (1990), Basic Local Alignment Search Tool.
Pearson & Lipman, PNAS, 85:2444, 1988, Improved Tools for Biological Sequence Comparison.
Frohman et. al, PNAS 85:8998–9002; 1988, Rapid Production of Full–Length cDNAs.
Graham and van der Eb, Virology 52:456 (1973), A New Technique for the Assay of Infectivity.
S. Subramani, et al., Mol & Cell. Biol., Sep. 1981, p. 854–864, Expression of the Mouse Dihydrofolate.
Towbin et al., PNAS, 76, 4350 (1979) Electrophoretic Transfer of Proteins from Polyacrylamide.
M. Kozak, J. Biol. Chem., vol. 266, No. 30, 19867–19870 (1991), Structural Features in Eukaryotic mRNAs.
Hosaka, et al., J. Biol, Chem., vol. 266, pp 12127–12130 (1997) Arg+X–Lys/Arg–Arg Motif As A Signal.

*Primary Examiner*—Deborah Crouch
*Attorney, Agent, or Firm*—Alan J. Morrison

[57] ABSTRACT

This invention provides proteins which selectively inhibit the proliferation of androgen-independent prostate cancer cells. This invention also provides a nucleic acid molecule encoding the instant proteins, including a nucleic acid molecule suitable for use in gene therapy for treating a subject afflicted with androgen-independent prostate cancer. This invention further provides a composition of matter which selectively kills androgen-independent prostate cancer cells, and comprises the instant proteins and a toxic moiety operably affixed thereto. Finally, the instant invention provides related pharmaceutical compositions and methods for treating androgen-independent prostate cancer.

1 Claim, 9 Drawing Sheets

FIG. 1

NUCLEOTIDE SEQUENCE OF GF-2H

```
   1  CGAGTCCCAG CTCTGAGCCG CAACCTGCAC AGCGATGCCC GGGCAAGAAC
  51  TCAGGACGCT GAATGGCTCT CAGATGCTCC TGGTGTTGCT GGTGCTCTCG
 101  TGGCTGCCGC ATGGGGGCGC CCTGTCTCTG GCCGAGGCGA GCCGCGCAAG
 151  TTTCCCGGGA CCCTCAGAGT TGCACTCCGA AGACTCCAGA TTCCGAGAGT
 201  TGCGGAAACG CTACGAGGAC CTGCTAACCA GGCTGCGGGC CAACCAGAGC
 251  TGGGAAGATT CGAACACCGA CCTCGTCCCG GCCCCTGCAG TCCGGATACT
 301  CACGCCAGAA GTGCGGCTGG GATCCGGGCG GCCCCTGCAC CTGCGTATCT
 351  CTCGGGCCGC CCTTCCTGCG GGGCTCCCCG CCACCTCCCG CCTTCACCGG
 401  GCTCTGTTCC GGCTGTCCCC GACGGCGTCA AGGTCGTGGG ACGTGACACG
 451  ACCGCTGCGG CGTCAGCTCA GCCTTGCAAG ACCCCAGGCG CCCGCGCTGC
 501  ACCTGCGACT GTCGCCGCCG CCGTCGCAGT CGGACCAACT GCTGGCAGAA
 551  TCTTCGTCCG CACGGGGCGC GCTGGAGTTG CACTTGCGGC CGCAAGCCCG
 601  CAGGGGGCGC CGCAGAGCGC GTGCGCACAC CGGGGACCAC TGTCCGCTCG
 651  GGCCCGGGCG TTGCTGCCGT CTGCCGCGTC CGGAGGTGTC GCTGGAAGAC
 701  CTGGGCTGGG CCGATTGGGT GCTGCACACG GGCGGCAAAC AAGTGACCAT
 751  GTGCATCGGC GCGTCCCCGA GCCAGTTCCG CGGACACGGT ATGCACGCGC
 801  AGATCAAGAC GAGCCTGCAC GGCCTGAAGC CCAGCGCCC  GCCAGCCCGA
 851  TGCTGCGTGC CCGCCAGCTA CAATCCCATG GTGCTCATTC AAAAGACCGA
 901  CACGGGGGTG TCGCTCCAGA CCTATGATGA CTTGTTAGCC AAAGACTGCC
 951  ACTGCATATG AGCAGTCCTG GTCCTTCCAC TGTGCACCTG CGCGGGGGAG
1001  GCGACCTCAG TTGTCCTGCC CTGTGGAATG GGCTCAAGGT TCCTGAGACA
1051  CCCGATTCCT GCCCAAACAG CTGTATTTAT TTAAAACTCT GATGATAAAA
1101  ATAAAGCTTG TCTTGAACTG TT
```

H-TGF-B2_P    1  ALDAAYCFR--NVQDNCCLRPLYIDFKRDLGWK-   31
H-TGF-B3_P    1  ALDTNYCFR--NLEENCCVRPLYIDFRQDLGWK-   31
B-TGF-B1_F    1  ALDTNYCFFS--STEKNCCVRPLYIDFRKDLGWK-  31
C-TGF-B4_F    1  DLDTDYCFGPGTDEKNCCVRPLYIDFRKDLQWK-   33
F-TGF-B5_P    1  GVGQEYCFG--NGPNCCVKPLYINFRKDLGWK-    31
ACTIVE2H2     1  ARNGDHCPLG---PGRCCRLHTVRASLEDLGWAD   31

H-TGF-B2_P   32  WIHEPKGYNANFCAGACPYLWSSDTQHSRVLSLY   65
H-TGF-B3_P   32  WVHEPKGYYANFCSGACPCPYLRSADTTHSTVLGLY 65
B-TGF-B1_F   32  WIHEPKGYHANFCLGPCPYIWSLDTQYSKVLALY   65
C-TGF-B4_F   34  WIHEPKGYMANFCMGPCPYIWSADTQYTKVLALY   67
F-TGF-B5_P   32  WIHEPKGYEANYCLGNCPYIWSMDTQYSKVLSLY   65
ACTIVE2H2    32  WVLSPREVQVTMCIGACPSQFRAANMHAQIKTSL   65

H-TGF-B2_P   66  NTINPEASASPCCVSQDLEPLTILYYIGKTPKIE   99
H-TGF-B3_P   66  NTLNPEASASPCCVPQDLEPLTILYYVGRTPKVE   99
B-TGF-B1_F   66  NQHNPGASAAPCCVPQALEPLPIVYYVGRKPKVE   99
C-TGF-B4_F   68  NQHNPGASAAPCCVPQTLDPLPIIYYVGRNVRVE  101
F-TGF-B5_P   66  NQNNPGASISPCCVPPDVLEPLPIIYYVGRTAKVE  99
ACTIVE2H2    66  HRLKPDTVPAPCCVPASYNPMVLIQKIDTGVSLQ   99

H-TGF-B2_P  100  QLSNMIVKSCKCS  112
H-TGF-B3_P  100  QLSNMVVKSCKCS  112
B-TGF-B1_F  100  QLSNMIVRSCKCS  112
C-TGF-B4_F  102  QLSNMVVRACKCS  114
F-TGF-B5_P  100  QLSNMVVRSCNCS  112
ACTIVE2H2   100  TYDDLLAKDCHCI  112
```

FIG. 2B

AMINO ACID SEQUENCE OF GF-2H

```
  1  MPGQELRTLN  GSQMLLVLLV  LSWLPHGGAL  SLAEASRASF  PGPSELHSED
 51  SRFRELRKRY  EDLLTRLRAN  QSWEDSNTDL  VPAPAVRILT  PEVRLGSGGH
101  LHLRISRAAL  PEGLPEASRL  HRALFRLSPT  ASRSWDVTRP  LRRQLSLARP
151  QAPALHLRLS  PPPSQSDQLL  AESSSARPQL  ELHLRPQAAR  GRRRARARNG
201  DHCPLGPGRC  CRLHTVRASL  EDLGWADWVL  SPREVQVTMC  IGACPSQFRA
251  ANMHAQIKTS  LHRLKPDTVP  APCCVPASYN  PMVLIQKTDT  GVSLQTYDDL
301  LAKDCHCI
```

PURIFICATION OF GF-2H

Purification of recombinant GF-2H

1&4. molecular weight standards
2. silver strain of GF-2H after FPLC purification
3. silver strain of GF-2H after HPLC purification
5. Western blot of GF-2H after HPLC purification with anti 2H peptide antibody

FIG. 4

AMINO ACID SEQUENCE OF MATURE GF-2H

```
  1 ARNGDHCPLG PGRCCRLHTV RASLEDLGWA DWVLSPREVQ VTMCIGACPS
 51 QFRAANMHAQ IKTSLHRLKP DTVPAPCCVP ASYNPMVLIQ KTDTGVSLQT
101 YDDLLAKDCH CI
```

NUCLEIC ACID MOLECULE ENCODING A PROTEIN GROWTH FACTOR FOR INHIBITING PROSTATE CANCER CELL GROWTH

This application claims priority of U.S. Provisional Application Serial No. 60/025,923, filed Sep. 11, 1996, the contents of which are hereby incorporated by reference.

FIELD OF THE INVENTION

This invention relates to proteins useful for treating subjects suffering from androgen-independent prostate cancer. This invention also relates to nucleic acid molecules, pharmaceutical compositions and methods for treating subjects with this disorder.

BACKGROUND OF THE INVENTION

Throughout this application, various publications are cited. The disclosure of these publications is hereby incorporated by reference into this application to describe more fully the state of the art to which this invention pertains.

Carcinoma of the prostate ("prostate cancer") is one of the most common types of malignancy. Among men 50 years of age or older, 30% harbor foci of cancer within the prostate. Only 1% of these afflicted men will be properly diagnosed with prostate cancer each year, highlighting a discrepancy between the high incidence of disease as revealed at autopsy and the much lower incidence revealed clinically. In 1992, 134,000 men in the United States were diagnosed with prostate cancer, and 32,000 died from this disease. Of all men clinically diagnosed with prostate cancer, more than half die within 10 years, and more than two-thirds suffer local or systemic progression despite therapy. Recently, testing for serum prostate-specific antigen (PSA) has allowed earlier detection, but it is unclear what the natural progression of the disease is in patients with elevated PSA but without large tumor burdens.

For cancer confined to the prostate, primary radiation or radical prostatectomy have roughly equivalent efficacy. Recurrences can be treated with radiation for primary surgery and, with difficulty, surgery for primary radiotherapy. Metastatic prostate lesions predominantly go to bone and can be treated by decreasing the androgen level in the subject. This can be done chemically by blocking adrenal and gonadal androgen production with drugs, or surgically by castration (which does not actually block adrenal production). The observation that patients will respond to such hormonal manipulation for only 6 months or so and then worsen suggests that the metastatic prostate lesions can become androgen-independent. This suggestion is supported by the finding that cultured cell lines from prostatic carcinomas contain mixed clones. These mixed clones are of three types: androgen-dependent, which survive only in the presence of exogenous androgen; androgen-sensitive, which remain alive in the absence of androgen and proliferate in its presence; and androgen-independent, which can survive as well as proliferate in the absence of androgens.

Among subjects suffering from prostate cancer, a significant population display clinical androgen-independence, i.e., the presence of prostate cancer cells which continue to proliferate even after therapeutic elimination of androgens. Surgery to remove a prostate tumor mass often results in the removal of androgen-independent cells along with other types of cells. However, surgery alone is rarely effective in this regard, since at least some androgen-independent cells remain. Accordingly, there exists a strong—and unmet—need for methods of treating prostate cancer using pharmaceutical agents which specifically inhibit the proliferation of androgen-independent cancer cells.

SUMMARY OF THE INVENTION

This invention provides a recombinant protein and an isolated protein, each of which selectively inhibits the proliferation of androgen-independent prostate cancer cells when contacted therewith under suitable conditions, and whose amino acid sequence comprises the amino acid sequence shown in FIG. 2, or functional derivative thereof.

This invention further provides a pharmaceutical composition for treating a subject afflicted with androgen-independent prostate cancer, comprising one of the instant proteins and a pharmaceutically acceptable carrier.

This invention further provides a nucleic acid molecule consisting essentially of a nucleic acid sequence encoding the amino acid sequence of FIG. 4 (SEQ ID NO:8) or functional derivative thereof, including, but not limited to, a nucleic acid molecule suitable for use in gene therapy for treating a subject afflicted with androgen-independent prostate cancer.

This invention further provides a pharmaceutical composition for treating a subject afflicted with androgen-independent prostate cancer, comprising the instant nucleic acid molecule suitable for use as a gene therapy vector and a pharmaceutically acceptable carrier.

This invention provides a composition of matter which selectively kills androgen-independent prostate cancer cells when contacted therewith under suitable conditions, and which comprises the instant protein and a toxic moiety operably affixed thereto.

This invention also provides a pharmaceutical composition for treating a subject afflicted with androgen-independent prostate cancer, comprising the instant composition of matter and a pharmaceutically acceptable carrier.

Finally, this invention provides methods of treating a subject afflicted with androgen-independent prostate cancer which comprise administering to the subject a therapeutically effective dose of one of the instant pharmaceutical compositions.

BRIEF DESCRIPTION OF THE FIGURES

FIG. 1 (SEQ ID NO:2) shows the DNA sequence of GF-2H.

FIG. 2A shows a comparison between the amino acid sequence of mature GF-2H protein (identified as "ACTIVE2H2") and those of other members of the TGF-beta family.

FIG. 2B shows the amino acid sequence of the immature GF-2H protein.

FIG. 4 (SEQ ID NO:8) shows the amino acid sequence of mature GF-2H.

DETAILED DESCRIPTION OF THE INVENTION

Figure 3A:
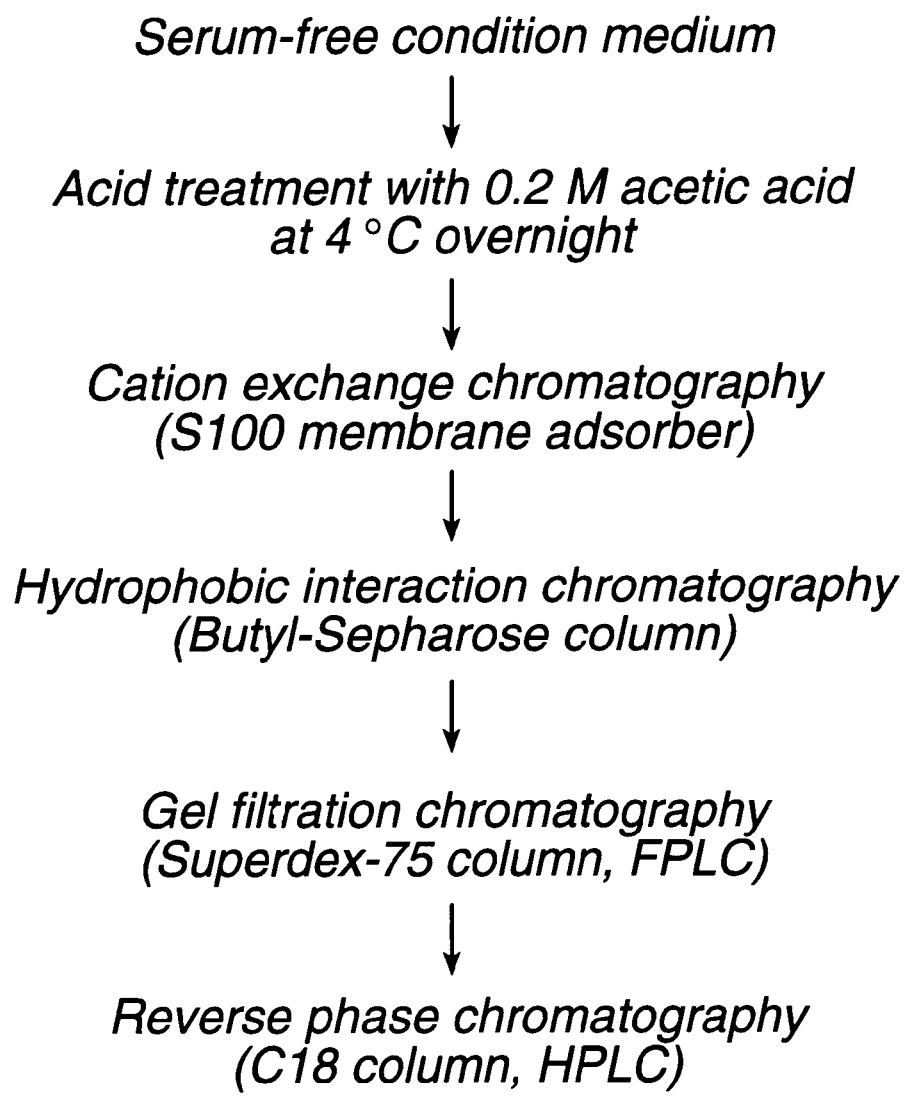
FIG. 3A shows a purification scheme of GF-2H.

Transforming growth factor type-beta (TGF-beta) represents a large family of multifunctional factors having diverse activities. TGF-beta is prototypic of a superfamily of growth, differentiation, and morphogenesis factors, such as inhibins, activins, Mulleria inhibiting substance, decapentaplegic product, and TGF-beta2. These factors are all structurally related to TGF-beta. Additionally, these factors, and others related to TGF-beta, appear to be involved in many processes of tissue development and repair. (J. Massague, Ann. Rev. Cell. Biol., 1990, 6:597–641).

Due to these diverse effects, TGF-beta-like proteins as a group may have potential for use as therapeutic agents for, inter alia, treating proliferative disorders. However, it is impossible to predict whether a TGF-beta-like protein having a known amino acid sequence will have an inhibitory effect on proliferating cells causing a particular disorder without also causing clinically unacceptable side effects, absent further empirical information. The proteins of the instant invention are TGF-beta-like based on their primary structures, and are capable of specifically inhibiting the proliferation of androgen-independent prostate cancer cells. However, absent additional empirical information, this specificity could not have been predicted based on amino acid sequence alone. Accordingly, the specific anti-prostate cancer activity of the instant TGF-beta-like proteins is most unexpected.

More specifically, this invention provides a recombinant protein which selectively inhibits the proliferation of androgen-independent prostate cancer cells when contacted therewith under suitable conditions, and whose amino acid sequence comprises the amino acid sequence shown in FIG. 4 (SEQ ID NO:8) or functional derivative thereof ("first protein"). In one embodiment, the first protein is selected from the proteins designated "rGF-2H", "recombinant GF-2H", or "recombinant mature GF-2H" discussed infra. In the preferred embodiment, the first protein is mature GF-2H.

This invention also provides an isolated protein which selectively inhibits the proliferation of androgen-independent prostate cancer cells when contacted therewith under suitable conditions, and whose amino acid sequence consists of the amino acid sequence shown in FIG. 4 (SEQ ID NO:8) or functional derivative thereof ("second protein"). In one embodiment, the second protein is selected from the group consisting of "GF-2H" and "mature GF-2H" discussed infra. In the preferred embodiment, the second protein is mature GF-2H.

As used herein, a recombinant protein is a protein which is obtained through the use of recombinant nucleic acid technology. Such recombinant protein's primary structure may be identical to that of its naturally occurring counterpart, or may contain additional amino acid residues. Additional residues may be present, for example, at the protein's N-terminal and/or C-terminal end. An isolated protein means any protein having a chemical milieu containing less than 50% protein impurities. In one embodiment, the isolated protein has a chemical milieu containing less than 10% protein impurities, and in the preferred embodiment, less than 1% protein impurities.

As used herein, a protein which is a "functional derivative" of the protein whose sequence is shown in FIG. 4 (SEQ ID NO:8) is a protein which possesses structural (i.e., amino acid sequence) and functional (i.e., selectively inhibits the proliferation of functional (i.e., selectively inhibits the proliferation of androgen-independent prostate cancer cells) similarity thereto. Structurally similar proteins include, by way of example, proteins differing from the protein of FIG. 4 (SEQ ID NO:8) by amino acid residue deletions, insertions, or conservative substitutions which do not substantially diminish the protein's ability to selectively inhibit the proliferation of androgen-independent prostate cancer cells. An example of a conservative amino acid substitution is the substitution of a leucine residue for an isoleucine residue.

As used herein, an "androgen-independent" prostate cancer cell is a prostate cancer cell which can survive (i.e. remain alive) as well as proliferate in the absence of androgens. As used herein, "proliferation" means the growth of cell population through cell division, and "selectively inhibit" androgen-independent cell proliferation means to reduce the in vitro rate of androgen-independent cell proliferation by at least 50% without reducing the in vitro rate of HeLa cell proliferation by more than 20% at saturating conditions and as measured at a suitable point in time (e.g. 72 hours after initial contact with the instant protein). In the preferred embodiment, the in vitro rate of androgen-independent cell proliferation is reduced by at least 90% without reducing the in vitro rate of HeLa cell proliferation by more than 10%. The rate of cell proliferation can readily be measured using known methods, such as the labeled thymidine incorporation method described hereinbelow.

Suitable conditions under which the first and second proteins selectively inhibit the proliferation of androgen-independent prostate cancer cells when contacted therewith means physiological conditions, i.e. the chemical milieu surrounding androgen-independent prostate cancer cells in situ which would permit the binding of an androgen-independent prostate cancer cell surface receptor to its corresponding naturally occurring ligand. Such conditions can readily be duplicated in vitro according to known methods.

This invention further provides a pharmaceutical composition for treating a subject afflicted with androgen-independent prostate cancer, comprising the first or second protein and a pharmaceutically acceptable carrier ("first pharmaceutical composition").

Pharmaceutically acceptable carriers are well known to those skilled in the art and include, but are not limited to, 0.01–0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

As used herein, "subject" means any animal or artificially modified animal capable of developing or sustaining prostate cancer. Artificially modified animals include, but are not limited to, mice, rats, dogs, guinea pigs, ferrets, rabbits, and primates. In one embodiment, the artificially modified animal is a mouse suffering from induced prostate cancer. Examples of such animals are known in the art (N. M. Greenberg, et al., P.N.A.S. U.S.A., 92:3439–3443 (1995); T. C. Thompson, et al., Cancer 71: 1165–1171 (1993)). In the preferred embodiment, the subject is a human.

This invention further provides a method of treating a subject afflicted with androgen-independent prostate cancer which comprises administering to the subject a therapeutically effective dose of the first pharmaceutical composition.

As used herein, administering may be effected or performed using any of the various methods known to those skilled in the art. The administering may comprise administering intravenously, intramuscularly, and subcutaneously.

A therapeutically effective dose of the first pharmaceutical composition is a dose sufficient to selectively inhibit the proliferation of androgen-independent prostate cancer cells in an afflicted subject. In the preferred embodiment, the treatment of an afflicted subject will comprise administering a plurality of therapeutically effective doses over a period of time. The dose and time period can be determined through known methods. In one embodiment, the therapeutically effective dose is from 0.1 ug/kg to 1 mg/kg, and in the preferred embodiment, the therapeutically effective dose is from 1 ug/kg to 100 ug/kg.

This invention further provides a nucleic acid molecule consisting essentially of a nucleic acid sequence encoding the amino acid sequence of FIG. 4 (SEQ ID NO:8) or functional derivative thereof.

In one embodiment, the nucleic acid molecule is an RNA molecule. In another embodiment, the nucleic acid molecule is a DNA molecule (e.g. cDNA or genomic DNA). The DNA molecule may comprise the nucleotide sequence shown in FIG. 1 (SEQ ID NO:2)

In an additional embodiment, the nucleic acid molecule is an expression vector. Numerous expression vectors may be employed. Such vectors, including plasmid vectors, cosmid vectors, bacteriophage vectors and other viruses, are well known in the art. For example, one class of vectors utilizes DNA elements which are derived from animal viruses such as bovine papilloma virus, polyoma virus, adenovirus, vaccinia virus, baculovirus, retroviruses (RSV, MMTV or MoMLV), Semliki Forest virus or SV40 virus. In the preferred embodiment, the vector is pCI. Additionally, host cells, regulatory elements, and transfection methods suitable for use in connection with this invention are well known in the art.

In a further embodiment, the nucleic acid molecule is a vector suitable for use in gene therapy for treating a subject afflicted with androgen-independent prostate cancer. Gene therapy vectors, and methods of delivering same, are well known in the art. Such delivery methods include, but are not limited to, delivery via adenovirus and cationic liposomes, as well as via naked DNA. Additionally, the instant vectors may be introduced into suitable cells ex vivo (e.g. peripheral blood mononuclear cells (PBMNC's)), which are then reintroduced into an afflicted subject. Methods for such ex vivo methods are known in the art.

This invention further provides a pharmaceutical composition for treating a subject afflicted with androgen-independent prostate cancer, comprising the instant nucleic acid molecule suitable for use in gene therapy and a pharmaceutically acceptable carrier ("second pharmaceutical composition").

This invention further provides a method of treating a subject afflicted with androgen-independent prostate cancer which comprises administering to the subject a therapeutically effective dose of the second pharmaceutical composition.

A therapeutically effective dose of the second pharmaceutical composition is a dose effective to cause cells in the subject to produce and secrete the protein encoded by the nucleic acid molecule therein, which protein in turn selectively inhibits the proliferation of androgen-independent prostate cancer cells in the subject. In one embodiment, the treatment of an afflicted subject will comprise administering a plurality of therapeutically effective doses over a period of time. The dose and time period can be determined through known methods. In one embodiment, the therapeutically effective dose of the second pharmaceutical composition is from $10^4$ to $10^{11}$ DNA molecules per subject, and in the preferred embodiment is from $10^5$ to $10^{10}$ DNA molecules per subject.

This invention also provides a composition of matter which selectively kills androgen-independent prostate cancer cells when contacted therewith under suitable conditions, and which comprises the first or second protein and a toxic moiety operably affixed thereto.

The toxic moiety may be a proteinaceous toxin. In one embodiment, the proteinaceous toxin is selected from the group consisting of ricin, tetanus toxin, diphtheria toxin, and subunits and fragments thereof. The toxic moiety may also be a radionuclide. In another embodiment, the toxic moiety is an $\alpha$- or $\beta$-emitting radionuclide including, but not limited to, $^{125}I$, $^{131}I$, $^{90}Y$, $^{212}Bi$. Methods for operably affixing toxic moieties to proteins are well known in the art.

This invention also provides a pharmaceutical composition for treating a subject afflicted with androgen-independent prostate cancer, comprising the instant composition of matter and a pharmaceutically acceptable carrier (the "third pharmaceutical composition").

This invention further provides a method of treating a subject afflicted with androgen-independent prostate cancer which comprises administering to the subject a therapeutically effective dose of the third pharmaceutical composition.

As used herein, to "selectively kill" androgen-independent cells means to kill at least 50% of androgen-independent cells in vitro without killing more than 20% of HeLa cells in vitro under saturating conditions as measured at a suitable point in time (e.g. 72 hours after initial contact with the instant composition). In the preferred embodiment, the instant composition kills at least 90% of androgen-independent cells in vitro without killing more than 10% of HeLa cells in vitro. Cell death can readily be measured using known methods including, for example, the Trypan Blue exclusion assay.

A therapeutically effective dose of the third pharmaceutical composition is a dose sufficient to selectively kill androgen-independent prostate cancer cells in an afflicted subject. In the preferred embodiment, the treatment of an afflicted subject will comprise administering a plurality of therapeutically effective doses over a period of time. The dose and time period can be determined through known methods. In one embodiment, the therapeutically effective dose is from 0.1 ug/kg to 1 mg/kg, and in the preferred embodiment, the therapeutically effective dose is from 1 ug/kg to 100 ug/kg.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Materials and Methods rIFN-$\gamma$ was purchased from Boehringer and Mannheim (>$2\times10^7$ units/mg). Expression vectors pCI, pcDNA3, and pSV2-dhfr were obtained from Promega, Invitrogen, and the American Type Cell Collection (ATCC), respectively. Cell culture media were obtained from GIBCO and BioWhittaker, and fetal bovine serum was obtained from Hyclone. Recombinant human TGF-beta was from R&D Systems. [$^3$H]thymidine was from DuPont NEN. S100 SartoBind cation membrane adsorber was from Sartorius. Chromatography columns and resins were from Pharmcia. Chemicals were from Fish and Sigma.

Cell lines and cell culture

All the cell lines were obtained from the ATCC. HeLa cells were maintained in MEM medium supplemented with 5% FBS, PC-3 and LNCaP cells in RPMI-1640 supplemented with 5% FBS, DU145 in EMEM supplemented with 10% FBS, HEL cells in RPMI supplemented with 10% FBS, HepG2 cells in MEM supplemented with 10% FBS and 1× non-essential amino acids, and BHK cells in DMEM supplemented with 5% FBS. Antibiotics (final concentration 50 ug/ml penicillin and 50 ug/ml streptomycin) were added to the culture media for all the cell lines.

Construction and screening of a subtractive cDNA library

HeLa cells (ATCC CCL185) were grown in Dulbecco's modified Eagle's medium (DMEM; GibcoBRL) supplemented with 10% fetal calf serum, 2 mM glutamine, 50 u/ml penicillin and 50 µg/ml streptomycin. HeLa cells were treated with recombinant human interferon-γ (IFN-γ) (Boehringer Mannheim) for 48 hours at a concentration of 2500 units/ml. Total RNA (RNAzol; Tell-Test) and poly (A)-selected RNA (FastTrack; Invitrogen) were isolated from mock and IFN-γ-treated HeLa cells following manufacturer's protocols.

For unidirectional cDNA library construction, cDNA's synthesized from 2 µgs of poly (A) RNA from untreated and IFN-γ-treated HeLa cells (48 hour treatment) were directionally cloned into the plasmids pGEM11Zf (Promega) and pT7T3D18U (Pharmacia), respectively. Subtractive hybridization, or more specifically, sense-strand cRNA and antisense cDNA syntheses, hybridization, separation of single-stranded cDNA from double-stranded cDNA/RNA hybrids by hydroxyapatite column and PCR amplification followed by subtractive library construction were performed according to known methods (Usui et. al, J. Neurosci., 14(8):4915–4926, 1994). The PCR-amplified subtracted cDNA's were directionally cloned into pT7T3D (Pharmacia).

To screen the subtracted cDNA library, 1000 cDNA's from this library were randomly picked and sequenced (see below). Clone #15558 (aka 2H) was found 6 times (per 1000 cDNA's analyzed) and therefore considered as a cDNA to be putatively differentially regulated by IFN-γ.

Cloning, DNA sequencing, and Computer Analysis

All sequencing was done on the Applied Biosystems 373 or 377 DNA sequencer in a single pass using T7 primer according to the manufacturer's protocol. Vector sequences were removed before analysis using the Sequencer program (Gene Codes Corporation). Inserts greater than 20 bp were compared via Blast (Altschul et. al, J. Mol. Biol., 215:40, 1990) to GenBank (version 92) for gene identification and were compared with each other via FastA (Pearson & Lipman, PNAS, 85:2444, 1988) to calculate the frequency of cDNA appearance in the subtracted cDNA library. Sequences containing Alu elements were excluded from the analysis. Blast analysis of 2H (clone #15558) indicated a significant homology to several members of the TGF-β superfamily. Clone #15558 was not full-length (i.e., it did not contain the entire coding region) and thus anchor PCR (Frohman et. al, PNAS 85:8998–9002; 1988) was implemented using 2 µg of poly (A) RNA (extracted from HeLa cells treated for 48 hours with IFN-γ) as a source for cDNA template synthesis. Two independent anchor PCR's were completed and the subsequent cDNA's were cloned and sequenced. An open reading frame was found with a stop codon upstream of this ATG indicating a full-length clone had been obtained.

Northern Blot Analysis

For RNA blots, 2 µg of poly (A) RNA extracted from HeLa cells (both mock control and HeLa cells treated with IFN-γ for 48 hours) were loaded per lane and subsequently resolved by electrophoresis on a 1.2% agarose, 1.2 M formaldehyde gel, transferred to a nitrocellulose membrane, and hybridized to a full-length $^{32}$P-labeled 2H cDNA probe. In addition, this $^{32}$P-labeled probe was hybridized to a human tissue RNA blot (Clontech).

Expression of rGF-2H

The entire coding region of GF-2H cDNA was subcloned into the EcoRI site of mammalian expression vector pCI (Promega) to generate the expression plasmid pCI-2H, which has a Kozak consensus sequence immediately upstream of the initiation codon ATG. DNA transfections were carried out by a modified calcium phosphate precipitation procedure (Graham and van der Eb, Virology 52:456 (1973)). For methotrexate (MTX) resistance, plasmid pSV2-dhfr (ATCC No. 37146; S. Subramani, et al., Mol. & Cell. Biol. September 1981, pg. 854–864)) or pZem229 (European Patent Appl. No. 0 319 944 A2, filed Jul. 12, 1988) was co-transfected with pCI-2H at a 1 to 4 ratio, and for G418 resistance, plasmid pcDNA3 (Invitrogen, #V790-20) was co-transfected with pCI-2H at a 1 to 4 ratio. Twenty-four hours after transfection, MTX (final concentration 1 uM) or G418 (final active concentration 1 mg/ml) was added to the culture media. Resistant colonies were randomly selected 10 days later. Serum-free condition culture media and cell lysates from selected clones were collected and subjected to Western blot analysis for expression and secretion of rGF-2H. Producing cell lines were established and maintained in 1 uM MTX or 1 mg/ml G418. Some of the MTX-resistant cell lines were subjected to 20 uM MTX to further amplify the transfected genes. The highest producing clone isolated was designated BHK-GF-2H #17 and used for the production of rGF-2H.

Purification of Recombinant Mature GF-2H

Serum-free condition medium from BHK-GF-2H #17 was collected and protease inhibitors were added at the following concentrations: 1 mM PMSF, 1 ug/ml leupeptin, 2 ug/ml pepstatin, 1 ug/ml aprotinin, and 1 mM EDTA. After centrifugation at 9000 rpm at 4° C. for 20 minutes to remove cell debris, the supernatant was acidified with acetic acid (0.2 M final concentration) at 4° C. overnight.

The supernatant was then loaded onto an S100 SartoBind cation membrane adsorber (Sartorius, #S100X) pre-equilibrated with 25 mM sodium phosphate pH 4.0 (Buffer A). The membrane adsorber was washed with Buffer A followed by Buffer A with 300 mM NaCl. rGF-2H was eluted from the membrane adsorber with 25 mM sodium phosphate pH 4.0 containing 500 mM NaCl and protease inhibitors (1 mM PMSF, 1 ug/ml leupeptin, 2 ug/ml pepstatin, 1 ug/ml aprotinin, and 1 mM EDTA).

After the addition of saturated $(NH_4)_2SO_4$ to a final concentration of 1 M, the pool was applied to an 8 ml Butyl Sepharose column pre-equilibrated with 25 mM $NaPO_4$, pH 7.0 containing 1 M NaCl and 1 M $(NH_4)_2SO_4$. The column was then washed with the same buffer and eluted with a linear 1-0 M gradient of both NaCl and $(NH_4)_2SO_4$ in 25 mM $NaPO_4$, pH 7.0. Fractions containing rGF-2H were pooled and concentrated using Centriprep-10 (Millipore).

The concentrated pool was applied to a Superdex-75 FPLC column (Pharmacia). The column was equilibrated and eluted with 20 mM Tris-HCl, pH 7.0, 100 mM KCl.

The fractions containing rGF-2H were applied to a Vydac C18 HPLC column (10-um particle size, 4.6×250 mm) equilibrated in 90% solvent A and 10% solvent B (solvent A contained 0.1% trifluoroacetic acid in water and solvent B was composed of 0.1% trifluoroacetic acid in acetonitrile). The column was eluted with a 10% to 90% linear gradient of solvent B. Fractions containing pure rGF-2H were lyophilized to dryness and re-suspended in 25 mM $NaPO_4$, pH 7.0 and stored at −70° C. in small aliquots.

Polyclonal Antibody to GF-2H

Peptide MHAQIKTSLHRLKPDTVPAPC, corresponding to residues 253 to 273 of pre-pro-GF-2H, was synthesized, coupled to keyhole limpet hemocyanin, emulsified in Freund's adjuvant, and injected into rabbits. The rabbit antisera were tittered against the peptide by ELISA.

Gel Electrophoresis and Western Blot Analysis

SDS-polyacrylamide gel electrophoresis was performed according to Laemmli, U.K. Nature, 227:680 (1970), and the gels were stained by either silver stain or Coomassie Brilliant Blue R-250. Western transfers were carried out as described (Towbin et al., PNAS, 76, 4350 (1979)). Immunostaining was performed using rabbit antibody against GF-2H peptide and horseradish peroxidase-conjugated anti-rabbit antibody (Bio-Rad).

N-Terminal Amino Acid and Mass Spectrometry Analysis

N-terminal sequence analysis was performed using an Applied Biosystems 470A protein sequencer equipped with an on-line phenylthiohydantoin analyzer (model 120A). Mass spectrometry analysis was performed using matrix-assisted laser desorption ionization mass spectrometry (MALDI-MS) on a Vestec 2000 MALDI-TOF-MS with a Lumonics NAG laser tuned at 355 nm.

Cell Proliferation Assay

Cells were seeded onto 96-well flat-bottom plates in 100 ul of corresponding complete culture at a density of 5,000 to 10,000 cells/well. After incubation overnight at 37° C., 5% $CO_2$, culture media were replaced with 100 ul of fresh medium supplemented with either 1% or 5% FBS containing an indicated concentration of rGF-2H or TGF-beta. After further incubation at 37° C., 5% $CO_2$ for a designated time period, cells were labeled with [$^3$H]thymidine (1 uCi/well) for 5 h at 37° C., 5% $CO_2$. At the end of incubation, the labeling media were removed, the cells were washed with PBS and incubated with 100 ul trypsin-EDTA at 37° C. for 10 minutes. Cells were then transferred from the culture plate onto a 96-well glass fiber plate (Unifilter plate, Parkard) using a cell harvester. The filter plate was washed, dried at 550° C. for 30 min., and each well was wetted with 40 ul of scintillation fluid (MicroScin-20, Parkard), and counted using a 96-well plate counter (TopCount, Parkard).

RESULTS

Cloning of IFN-γ-Inducible Genes From HeLa Cells

The full-length clone of GF-2H-encoding DNA spans 1122 base pairs (FIG. 1 (SEQ ID NO:2)). An initiator methionine (base pairs 35–37) was identified by the following criteria: (a) there was an in-frame stop codon (base pairs 14–16) upstream of this methionine; (b) the amino acid sequence was consistent with Kozak's consensus sequence (Kozak, J. Biol. Chem., Vol. 266., No. 30, 19867–19870 (1991); and (c) this methionine was followed by a putative signal peptide.

A stop codon was found at base pairs 959–961, indicating the end of the open reading frame (FIG. 1 (SEQ ID NO:2)). This corresponds to an open reading frame of 927 base pairs. The 3' noncoding region contains a poly adenylation signal, AATAAA (base pairs 1100–1105), and two instability motifs, ATTTA (base pair 1075–1079), found in the 3'-noncoding regions of short-lived mRNAs.

Expression of GF-2H mRNA

Figure 3B:
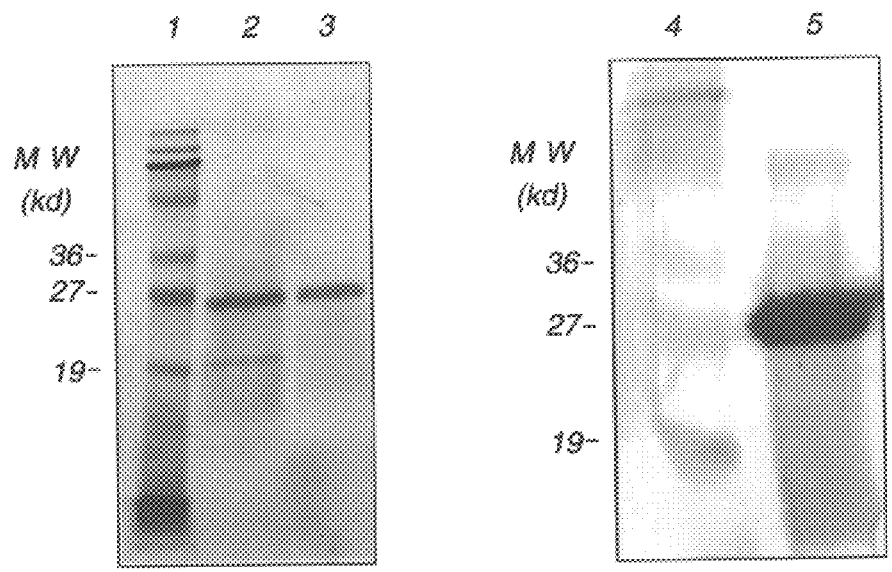
FIG. 3B shows a purification scheme of rGF-2H.

Northern blot analysis was performed to determine the approximate length of the GF-2H transcript and to show the pattern of MRNA tissue expression. Northern blots were performed using a 1.2 kb fragment as a probe. Hybridization showed a major transcript at approximately 1.4 kb only in HeLa cells treated with IFN-γ and not in untreated HeLa cells (FIG. 3A). Screening of different tissues showed that the GF-2H mRNA is detectable in placenta, prostate, liver, kidney, fetal lung, and fetal kidney (FIG. 3B). The relative amounts of mRNA in placenta and prostate were greater than those in other tissues (FIG. 3B).

Analysis of the Putative GF-2H Protein

The predicted GF-2H gene product is 308 amino acid residues long with a calculated molecular mass of 34.1 kDa. Both nucleotide and predicted protein sequences of GF-2H have been compared to those in sequence data banks. A Blast search of protein sequence databases revealed a significant level of homology between the putative GF-2H protein and the TGF-beta superfamily. The entire GF-2H protein shows 28.2% identity to the precursor form of human Gdf1, while the C-terminal one third of GF-2H protein shows 30.4% identity to the mature form of Drosophila dpp protein. When the sequence of the C-terminal one third of GF-2H protein was aligned with those of TGF-beta superfamily members for maximum similarity using the PILEUP program, it was observed that all of the nine conserved cysteines as well as some other conserved residues in the TGF-beta proteins (Hosaka, et al., J. Biol. Chem., Vol. 266, pp 12127–12130 (1991)) were present in the C-terminal one third of GF-2H protein.

Like most members of the TGF-beta superfamily, the GF-2H protein contains an N-terminal signal sequence and potential sites for N-linked and O-linked glycosylation. There is a cluster of basic residues which provide potential cleavage sites from which to generate the mature form from the precursor (Hosaka, et al. (1991)). FIG. 2A shows the amino acid sequence of the immature GF-2H protein. FIG. 2B shows a comparison between the amino acid sequence of mature GF-2H protein and those of other members of the TGF-beta family.

Expression of Recombinant GF-2H Proteins

To express recombinant GF-2H, the entire coding region of GF-2H cDNA was inserted into mammalian expression vector pCI to generate pCI-2H. Stable transfected BHK cell lines were obtained by co-transfecting BHK tk⁻ts13 cells with plasmids pCI-2H and pSV2-dhfr or pZem229 containing an expression unit for mouse DHFR, which allowed for selection of transfectants with MTX. Expression of GF-2H by these cell lines was examined by Western blot analysis using anti-GF-2H peptide antibody (data not shown). One of these cell lines, BHK-2H-#17, was used to further characterize expression of rGF-2H.

When the conditioned medium was fractionated on SDS-PAGE under reducing conditions and blotted with anti-GF-2H peptide antibody, a band with an apparent molecular weight of 13 kd was observed in BHK-2H-#17 cells (FIG. 4 (SEQ ID NO:8), lane 5). This band was not seen in the control BHK cells (FIG. 4 (SEQ ID NO:8), lane 4). On some occasions, another band with an apparent molecular weight of 39 kd was also observed in the BHK-2H-#17 cells, but not in the control BHK cells (data not shown). When the conditioned medium was fractionated on SDS-PAGE under non-reducing conditions and blotted with anti-GF-2H peptide antibody, a band with an apparent molecular weight of 25 kd was observed in BHK-2H-#17 cells (FIG. 4 (SEQ ID NO:8), lane 3), but not in the control BHK cells (FIG. 4 (SEQ ID NO:8), lane 2). These results suggest that GF-2H is expressed, processed to a smaller form, and secreted into the culture medium by BHK-2H-#17 cells. The secreted GF-2H is most likely a disulfide-linked dimer (25 kDa) of the 13 kd protein. The 39 kd form is most likely to be the full-length GF-2H with some post translational modification, such as glycosylation, since the predicted molecular weight for the full-length GF-2H is 34 kd.

Purification and Characterization of Recombinant GF-2H

Conditioned medium from BHK-2H-#17 was used to purify the processed mature form of rGF-2H by a four-step purification protocol developed specifically for rGF-2H (see discussion supra). Using this protocol, mature rGF-2H was purified to greater than 95% as judged by SDS-PAGE and silver stain analysis (data not shown).

Figure 5:
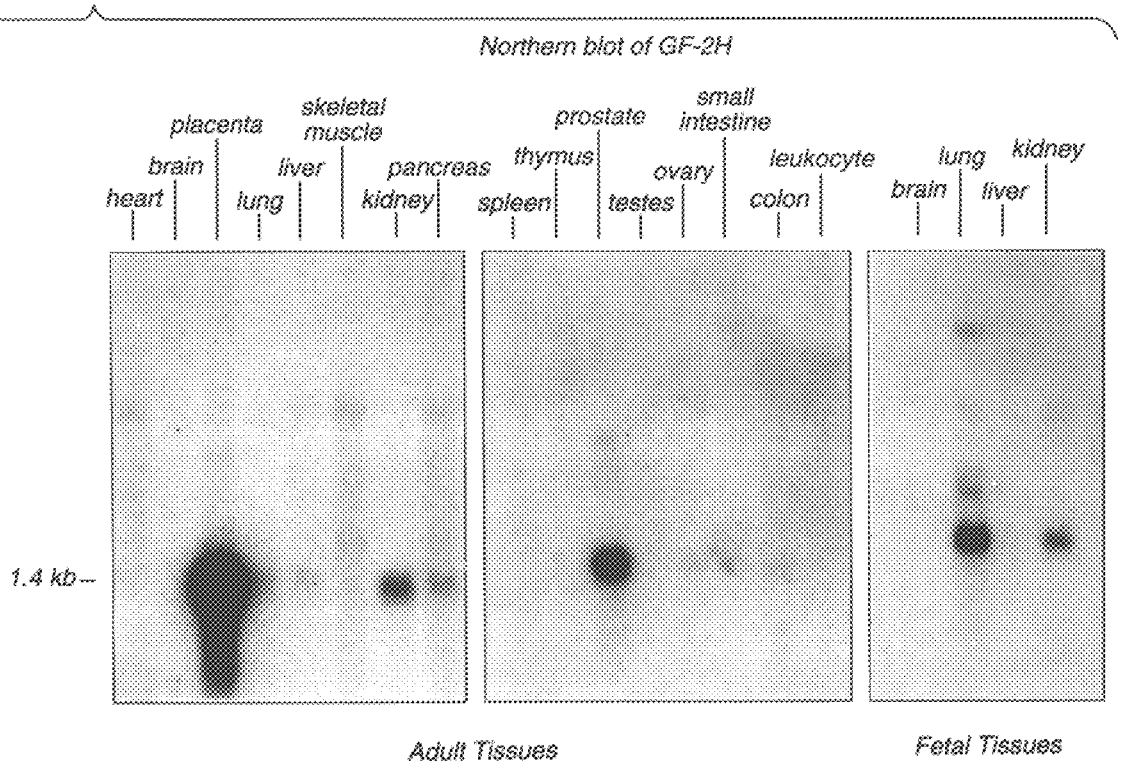
FIG. 5 shows the expression of GF-2H-encoding mRNA in different tissues.
Figure 6:
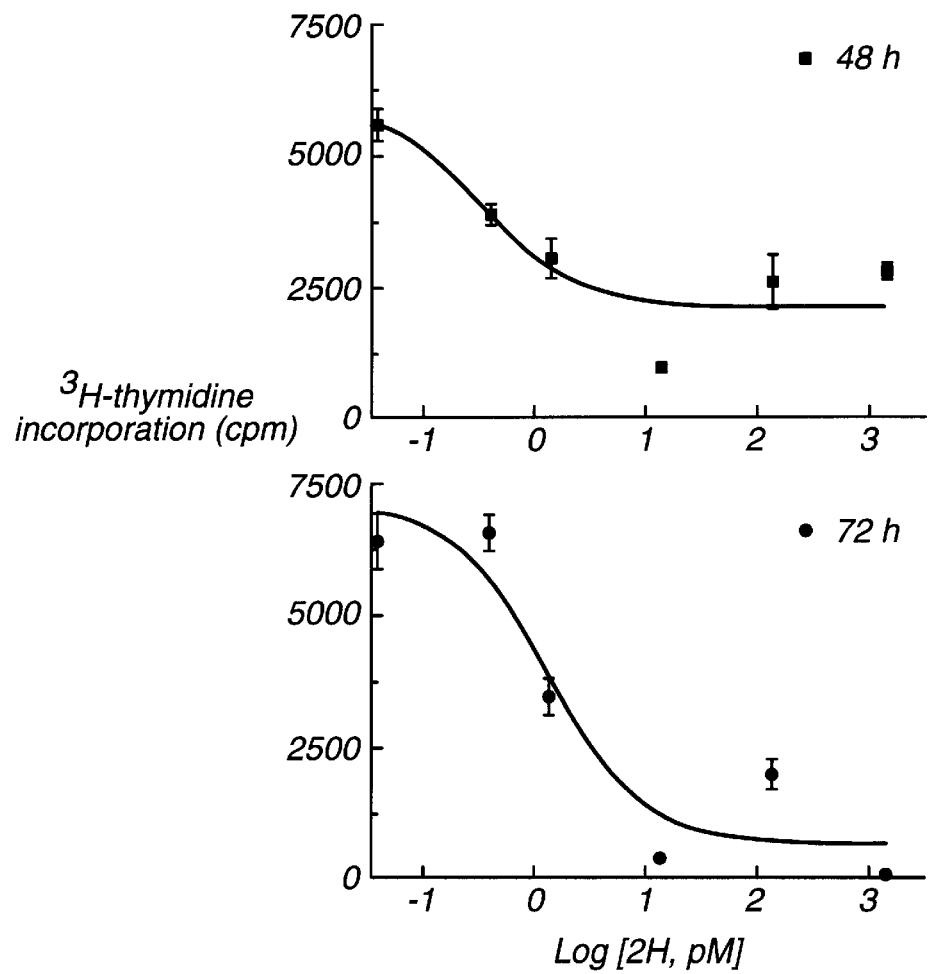
FIG. 6 shows the modulation of prostate cancer cell line PC-3 by mature GF-2H.

When analyzed by SDS-PAGE under reducing conditions, purified recombinant mature GF-2H was detected as a 13 kd band, while under non-reducing conditions it was detected as a 25 kd band (FIG. 5). The molecular mass of mature rGF-2H was also determined to be 25 kd by mass spectrum analysis (data not shown). N-terminal amino acid sequence analysis of purified recombinant mature GF-2H showed that: the mature rGF-2H sequence begins at residue 197 of the full-length GF-2H (FIG. 6). The calculated molecular weight of the polypeptide from residue 197 to 308 of the full-length rGF-2H is 12.3 kd. These results demonstrate that the mature rGF-2H contains the C-terminal portion of the full-length rGF-2H, residues 197 to 308, linked together by disulfide bond(s).

Effect of rGF-2H on Cell Proliferation

Purified rGF-2H was tested on a variety of human cell lines to examine its effects on cell proliferation. Cells were plated out, incubated with various concentrations of rGF-2H for 24 to 96 hours, and labeled with [$^3$H]thymidine, as described supra. Human TGF-beta2 was also tested on these cell lines in parallel with rGF-2H in order to compare its effects with that of rGF-2H.

Figure 7:
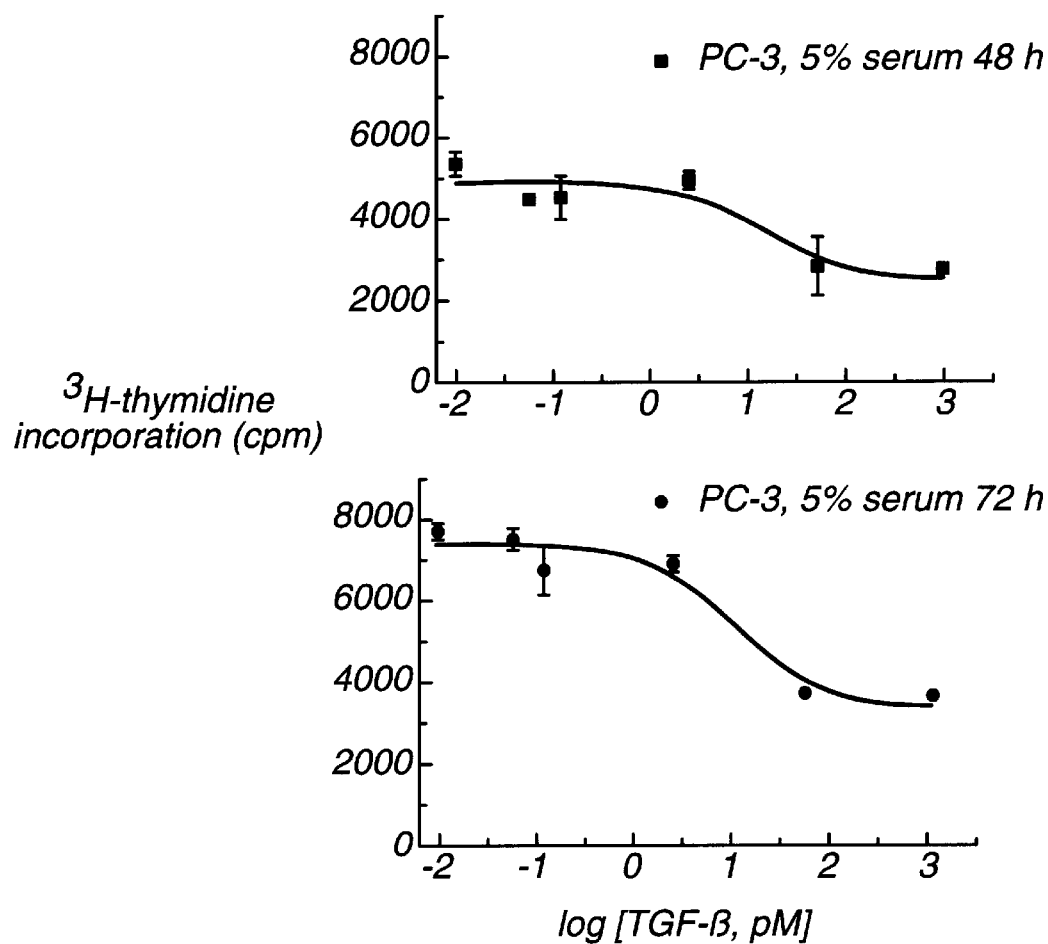
FIG. 7 shows the modulation of prostate cancer cell line PC-3 by mature TGF-beta.

Recombinant GF-2H showed a dose- and time-dependent inhibition of [$^3$H]thymidine incorporation by PC-3 cells, an androgen-independent prostate cancer cell line. This inhibitory effect was first observed after a 48-hour incubation period (FIG. 6) and continued to be seen after a 96-hour incubation period, at which time significant cell death started to occur. The maximum inhibition, approximately 90% compared with that of the control (without rGF-2H), was observed after a 72-hour incubation at $1.4 \times 10^{-11}$ M rGF-2H (FIG. 6). When TGF-beta was tested on PC-3 cells under the same conditions, a similar dose- and time-dependent inhibition to that of rGF-2H was also observed. However, the maximum inhibition seen with TGF-beta was only 52% when compared to the control (FIG. 7). Similar to PC-3 cells, dose- and time-dependent inhibition of [$^3$H] thymidine incorporation by rGF-2H and TGF-beta were seen with DU145 cells, another androgen-independent prostate cancer cell line (Table 1). The maximum inhibition by rGF-2H and TGF-beta was 60% and 80%, respectively, compared with that of controls (data not shown).

TABLE 1

Effects of GF-2H on Proliferation of Selected Human Cell Lines

| Cell Line | rGF-2H | TGF-beta |
|---|---|---|
| PC-3 (androgen-independent prostate carcinoma) | inhibition | inhibition |
| DU145 (androgen-independent prostate carcinoma) | inhibition | inhibition |
| LNCaP (androgen-dependent prostate carcinoma) | no effect | inhibition |
| HepG2 (hepatoma) | no effect | inhibition |
| HEL (erythroleukemia) | no effect | inhibition |
| HeLa (cervix epitheloid carcinoma) | no effect | slight inhibition |
| Caov-3 (ovary adeno-carcinoma) | no effect | no effect |

As summarized in Table 1, rGF-2H had no effect on [$^3$H]thymidine incorporation by LNCaP, Hep G2, or HEL cells. In contrast, TGF-beta inhibited [$^3$H]thymidine incorporation by these cells. Neither rGF-2H nor TGF-beta showed significant effects on [$^3$H]thymidine incorporation by HeLa and Caov-3 cells. In short, rGF-2H was shown to specifically inhibit the proliferation of androgen-independent prostate cancer cells, unlike TGF-beta which shows inhibitory behavior on additional cell lines.

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 21 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

Met His Ala Gln Ile Lys Thr Ser Leu His Arg Leu Lys Pro Asp Thr
1            5              10             15

```
Val Pro Ala Pro Cys
        20

(2) INFORMATION FOR SEQ ID NO:2:

(i) SEQUENCE CHARACTERISTICS:
        (A) LENGTH: 1122 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

CGAGTCCCAG CTCTGAGCCG CAACCTGCAC AGCGATGCCC GGGCAAGAAC TCAGGACGCT      60

GAATGGCTCT CAGATGCTCC TGGTGTTGCT GGTGCTCTCG TGGCTGCCGC ATGGGGCGC      120

CCTGTCTCTG GCCGAGGCGA GCCGCGCAAG TTTCCCGGGA CCCTCAGAGT TGCACTCCGA     180

AGACTCCAGA TTCCGAGAGT TGCGGAAACG CTACGAGGAC CTGCTAACCA GGCTGCGGGC     240

CAACCAGAGC TGGGAAGATT CGAACACCGA CCTCGTCCCG GCCCCTGCAG TCCGGATACT     300

CACGCCAGAA GTGCGGCTGG GATCCGGCGG CCACCTGCAC CTGCGTATCT CTCGGGCCGC     360

CCTTCCTGAG GGGCTCCCCG AGGCCTCCCG CCTTCACCGG GCTCTGTTCC GGCTGTCCCC     420

GACGGCGTCA AGGTCGTGGG ACGTGACACG ACCGCTGCGG CGTCAGCTCA GCCTTGCAAG     480

ACCCCAGGCG CCCGCGCTGC ACCTGCGACT GTCGCCGCCG CCGTCGCAGT CGGACCAACT     540

GCTGGCAGAA TCTTCGTCCG CACGGCCCCA GCTGGAGTTG CACTTGCGGC CGCAAGCCGC     600

CAGGGGGCGC CGCAGAGCGC GTGCGCGCAA CGGGGACCAC TGTCCGCTCG GCCCCGGGCG     660

TTGCTGCCGT CTGCACACGG TCCGCGCGTC GCTGGAAGAC CTGGGCTGGG CCGATTGGGT     720

GCTGTCGCCA CGGGAGGTGC AAGTGACCAT GTGCATCGGC GCGTGCCCGA GCCAGTTCCG     780

GGCGGCAAAC ATGCACGCGC AGATCAAGAC GAGCCTGCAC CGCCTGAAGC CCGACACGGT     840

GCCAGCGCCC TGCTGCGTGC CCGCCAGCTA CAATCCCATG GTGCTCATTC AAAAGACCGA     900

CACCGGGGTG TCGCTCCAGA CCTATGATGA CTTGTTAGCC AAAGACTGCC ACTGCATATG     960

AGCAGTCCTG GTCCTTCCAC TGTGCACCTG CGCGGGGAG GCGACCTCAG TTGTCCTGCC     1020

CTGTGGAATG GGCTCAAGGT TCCTGAGACA CCCGATTCCT GCCCAAACAG CTGTATTTAT     1080

TTAAAACTCT GATGATAAAA ATAAAGCTTG TCTTGAACTG TT                       1122

(2) INFORMATION FOR SEQ ID NO:3:

(i) SEQUENCE CHARACTERISTICS:
        (A) LENGTH: 112 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Trp Lys Trp
                20                  25                  30

Ile His Glu Pro Lys Gly Tyr Asn Ala Asn Phe Cys Ala Gly Ala Cys
            35                  40                  45

Pro Tyr Leu Trp Ser Ser Asp Thr Gln His Ser Arg Val Leu Ser Leu
        50                  55                  60
```

Tyr Asn Thr Ile Asn Pro Glu Ala Ser Ala Ser Pro Cys Cys Val Ser
65                  70                  75                  80

Gln Asp Leu Glu Pro Leu Thr Ile Leu Tyr Tyr Ile Gly Lys Thr Pro
                85                  90                  95

Lys Ile Glu Gln Leu Ser Asn Met Ile Val Lys Ser Cys Lys Cys Ser
            100                 105                 110

(2) INFORMATION FOR SEQ ID NO:4:

(i) SEQUENCE CHARACTERISTICS:
        (A) LENGTH: 112 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
                20                  25                  30

Val His Glu Pro Lys Gly Tyr Tyr Ala Asn Phe Cys Ser Gly Pro Cys
                35                  40                  45

Pro Tyr Leu Arg Ser Ala Asp Thr Thr His Ser Thr Val Leu Gly Leu
50                  55                  60

Tyr Asn Thr Leu Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
                85                  90                  95

Lys Val Glu Gln Leu Ser Asn Met Ile Val Lys Ser Cys Lys Cys Ser
            100                 105                 110

(2) INFORMATION FOR SEQ ID NO:5:

(i) SEQUENCE CHARACTERISTICS:
        (A) LENGTH: 112 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
                20                  25                  30

Ile His Glu Pro Lys Gly Tyr His Ala Asn Phe Cys Leu Gly Pro Cys
                35                  40                  45

Pro Tyr Ile Trp Ser Leu Asp Thr Gln Tyr Ser Lys Val Leu Ala Leu
50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110

(2) INFORMATION FOR SEQ ID NO:6:

(i) SEQUENCE CHARACTERISTICS:
    (A) LENGTH: 114 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:6:

```
Asp Leu Asp Thr Asp Tyr Cys Phe Gly Pro Gly Thr Asp Glu Lys Asn
 1               5                  10                  15

Cys Cys Val Arg Pro Leu Tyr Ile Asp Phe Arg Lys Asp Leu Gln Trp
                20                  25                  30

Lys Trp Ile His Glu Pro Lys Gly Tyr Met Ala Asn Phe Cys Met Gly
            35                  40                  45

Pro Cys Pro Tyr Ile Trp Ser Ala Asp Thr Gln Tyr Thr Lys Val Leu
        50                  55                  60

Ala Leu Tyr Asn Gln His Asn Pro Gly Ala Ser Ala Ala Pro Cys Cys
65                  70                  75                  80

Val Pro Gln Thr Leu Asp Pro Leu Pro Ile Ile Tyr Tyr Val Gly Arg
                85                  90                  95

Asn Val Arg Val Glu Gln Leu Ser Asn Met Val Val Arg Ala Cys Lys
                100                 105                 110

Cys Ser
```

(2) INFORMATION FOR SEQ ID NO:7:

(i) SEQUENCE CHARACTERISTICS:
        (A) LENGTH: 112 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

```
Gly Val Gly Gln Glu Tyr Cys Phe Gly Asn Asn Gly Pro Asn Cys Cys
 1               5                  10                  15

Val Lys Pro Leu Tyr Ile Asn Phe Arg Lys Asp Leu Gly Trp Lys Trp
                20                  25                  30

Ile His Glu Pro Lys Gly Tyr Glu Ala Asn Tyr Cys Leu Gly Asn Cys
            35                  40                  45

Pro Tyr Ile Trp Ser Met Asp Thr Gln Tyr Ser Lys Val Leu Ser Leu
        50                  55                  60

Tyr Asn Gln Asn Asn Pro Gly Ala Ser Ile Ser Pro Cys Cys Val Pro
65                  70                  75                  80

Asp Val Leu Glu Pro Leu Pro Ile Ile Tyr Tyr Val Gly Arg Thr Ala
                85                  90                  95

Lys Val Glu Gln Leu Ser Asn Met Val Val Arg Ser Cys Asn Cys Ser
                100                 105                 110
```

(2) INFORMATION FOR SEQ ID NO:8:

(i) SEQUENCE CHARACTERISTICS:
        (A) LENGTH: 112 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

```
Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

(2) INFORMATION FOR SEQ ID NO:9:

(i) SEQUENCE CHARACTERISTICS:
        (A) LENGTH: 308 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

```
Met Pro Gly Gln Glu Leu Arg Thr Leu Asn Gly Ser Gln Met Leu Leu
1               5                   10                  15

Val Leu Leu Val Leu Ser Trp Leu Pro His Gly Gly Ala Leu Ser Leu
            20                  25                  30

Ala Glu Ala Ser Arg Ala Ser Phe Pro Gly Pro Ser Glu Leu His Ser
        35                  40                  45

Glu Asp Ser Arg Phe Arg Glu Leu Arg Lys Arg Tyr Glu Asp Leu Leu
    50                  55                  60

Thr Arg Leu Arg Ala Asn Gln Ser Trp Glu Asp Ser Asn Thr Asp Leu
65                  70                  75                  80

Val Pro Ala Pro Ala Val Arg Ile Leu Thr Pro Glu Val Arg Leu Gly
                85                  90                  95

Ser Gly Gly His Leu His Leu Arg Ile Ser Arg Ala Ala Leu Pro Glu
            100                 105                 110

Gly Leu Pro Glu Ala Ser Arg Leu His Arg Ala Leu Phe Arg Leu Ser
        115                 120                 125

Pro Thr Ala Ser Arg Ser Trp Asp Val Thr Arg Pro Leu Arg Arg Gln
    130                 135                 140

Leu Ser Leu Ala Arg Pro Gln Ala Pro Ala Leu His Leu Arg Leu Ser
145                 150                 155                 160

Pro Pro Pro Ser Gln Ser Asp Gln Leu Leu Ala Glu Ser Ser Ser Ala
                165                 170                 175

Arg Pro Gln Leu Glu Leu His Leu Arg Pro Gln Ala Ala Arg Gly Arg
            180                 185                 190

Arg Arg Ala Arg Ala Arg Asn Gly Asp His Cys Pro Leu Gly Pro Gly
        195                 200                 205

Arg Cys Cys Arg Leu His Thr Val Arg Ala Ser Leu Glu Asp Leu Gly
    210                 215                 220

Trp Ala Asp Trp Val Leu Ser Pro Arg Glu Val Gln Val Thr Met Cys
```

```
225                 230                 235                 240
Ile Gly Ala Cys Pro Ser Gln Phe Arg Ala Ala Asn Met His Ala Gln
                245                 250                 255
Ile Lys Thr Ser Leu His Arg Leu Lys Pro Asp Thr Val Pro Ala Pro
                260                 265                 270
Cys Cys Val Pro Ala Ser Tyr Asn Pro Met Val Leu Ile Gln Lys Thr
                275                 280                 285
Asp Thr Gly Val Ser Leu Gln Thr Tyr Asp Asp Leu Leu Ala Lys Asp
        290                 295                 300
Cys His Cys Ile
305

(2) INFORMATION FOR SEQ ID NO:10:

(i) SEQUENCE CHARACTERISTICS:
        (A) LENGTH: 112 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
                35                  40                  45

Pro Ser Gln Phe Arg Ala Ala Asn Met His Ala Gln Ile Lys Thr Ser
        50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
                100                 105                 110
```

What is claimed is:

1. An isolated nucleic acid molecule comprising the nucleotide sequence of SEQ ID NO:2.

\* \* \* \* \*